(12) United States Patent
Rutenberg et al.

(10) Patent No.: US 8,501,425 B1
(45) Date of Patent: Aug. 6, 2013

(54) DETECTION OF CHRONIC AND ACUTE PULMONARY INFLAMMATION

(75) Inventors: Mark Rutenberg, Suffern, NY (US);
Richard Scott, Suffern, NY (US);
Stephen Frist, Maleh Adumim (IL)

(73) Assignee: Mark Rutenberg, Suffern, NY (US)

( * ) Notice: Subject to any disclaimer, the term of this patent is extended or adjusted under 35 U.S.C. 154(b) by 367 days.

(21) Appl. No.: 12/817,963

(22) Filed: Jun. 17, 2010

Related U.S. Application Data

(60) Provisional application No. 61/187,883, filed on Jun. 17, 2009.

(51) Int. Cl.
*G01N 33/48* (2006.01)

(52) U.S. Cl.
USPC .......................................................... 435/7.24

(58) Field of Classification Search
None
See application file for complete search history.

*Primary Examiner* — James Martinell

(74) *Attorney, Agent, or Firm* — Levisohn Berger LLP

(57) ABSTRACT

A method and apparatus for analyzing a sputum cytology preparation. The sputum sample is fixed on a microscope slide and analyzed by a microscope combined with an image acquisition system and a computer having an image recognition system. The image recognition system detects mobile cells that are implicated in the body's inflammatory response and counts how many of such cells are on the slide. The computer generates an absolute number of such cells and percentage values for such cells out the total number of mobile cells classified. The computer then utilizes the absolute numbers, the ratios of mobile cells with respect to each other—or a combination of both to generate a score. The score represents a probabilistic determination of inflammation.

5 Claims, 3 Drawing Sheets

DETECTION OF CHRONIC AND ACUTE PULMONARY INFLAMMATION

RELATED APPLICATIONS

This application claims the benefit of U.S. Provisional Patent Appl. Ser. No. 61/187,883, filed Jun. 17, 2009—the contents of which are incorporated by reference herein.

FIELD OF THE INVENTION

The invention relates to the field of computer-assisted diagnosis of cytological preparations, more specifically to a method and apparatus for determining a likelihood of pulmonary inflammation.

BACKGROUND OF THE INVENTION

Inflammation occurs as part of a tissue's local response to pathogen invasion, injury or other irritation. The immune response to such injurious conditions is characterized by, both, physiological and cellular/molecular defensive processes of recognizing and destroying invasion or injury.

In the physiological process, blood vessels in the affected region become dilated and capillary permeability becomes increased. This inflammatory response allows for increased blood flow to an affected region and for specialized hematopoietic and mobile tissue cells to be quickly and abundantly dispatched to their site of action.

The cellular response includes the recruitment of various specialized cells of the body's immune system to destroy or otherwise neutralize an offending or injurious agent.

There are generally two stages associated with inflammation—namely "acute" and "chronic" stages. The early stage is termed the acute stage and is the body's initial response to a tissue irritation. If such irritation persists, the immune response enters into the chronic stage. There are specialized white blood cells that tend to be at elevated levels in the acute stage and different ones that tend to exist at elevated levels in the chronic stage.

Lung tissue is susceptible to inflammation, but because of physical constraints, it is extremely difficult to detect. One possible method of detection is through a bronchoscope examination, whereby a clinician may detect inflammation based on visual inspection. Such visual inspection is uncomfortable and intrusive and it suffers from poor sensitivity.

One well-known modality employed to assess acute and chronic pulmonary inflammation is sputum cytology. In this modality, a sample of sputum (produced in the lungs and in the airways leading thereto) is examined under a microscope to determine whether or not inflammatory cells are present. Sputum cytology, however, suffers from numerous shortcomings as described below.

The normal cellular elements in the distal pulmonary tree, bronchioles and alveoli, are columnar ciliated epithelium, nonciliated epithelium (Clara cells), flat epithelial type 1 pneumocytes, goblet cells, and endocrine argentaffin cells. Mobile cells from the blood and interstitial space are also present. These consist of polymorphonuclear leukocytes, lymphocytes, plasma cells, eosinophils, mast cells and macrophages.

Pulmonary inflammation is characterized by an alteration in the number and proportion of the mobile cells. The current microscopic method for assessing inflammation is based on a pathologist's qualitative interpretation of the sputum cytology specimen. By inspecting the slide, the pathologist forms an impression as to what cells lines are present and whether they are increased/normal/decreased in number on an absolute basis, and whether they are increased/normal/decreased in relation to the other cellular constituents.

This type of perceptual analysis—difficult in any situation—is rendered more difficult in the specific circumstances of sputum cytology. Firstly, the cell types are not uniformly dispersed. There are always areas of increased density and other areas of paucity of each cell line. This is the result of the cells not being maintained in a uniform suspension. They are preserved in a substrate, mucus-containing sputum, composed of many non-cellular elements, such as fibrin. Groups of cells may be attracted to the substrate, others repelled. Some groups may be physically entrapped. This confusing scenario, not observed in toto but rather field by field, is not amenable to meaningful or reproducible evaluation. In a recent study, Asthma Research Group, Dept of Medicine, St. Joseph's Hospital and McMaster University, Hamilton, Ontario, CANADA, the authors examined the extent of agreement between clinical judgment of sputum cell counts and actual counts in asthmatic patients (Cohen's Kappa) and the possible predictors of agreement (multiple logistic regression). Sixty-seven of the 76 sputum samples were suitable for analysis. Agreement between expected and actual cell counts occurred in 30/67 patients. The overall agreement for the different cell types was poor (estimated K=0.14, 95% confidence interval (CI)=0.02, 0.26). (Parameswaran et al, 2000).

Another shortcoming of the current microscopic analysis derives from its lack of quantification. The subjective nature of the diagnosis does not allow for comparison of progression or regression over time. Once the diagnosis of pulmonary inflammation is established, it is important to follow the progress of the disease and its response to therapy. A qualitative microscopic diagnosis limits the ability to accomplish this important objective.

SUMMARY OF THE INVENTION

To address the problems associated with traditional sputum cytology, the current invention utilizes a microscope combined with a computer image processing system to identify and generate counts of inflammatory cells found within a sputum cytology preparation. This novel quantitative analysis can be used to identify individuals with either acute or chronic pulmonary inflammation—distinguishing between the two.

The image recognition system, using well known morphological characteristics, detects the presence of at least four important white blood cell types, namely: polymorphonuclear leukocytes (PMN's), macrophages, lymphocytes and plasma cells in a sample of sputum. The system then counts the number of each of these cell types in the sample vis-à-vis the total number of mobile cells ("mobile cells" interchangeably herein) on the slide to determine a percentage value for each of the cell types. Using the percentage values for at least two of the white blood cell types, a probabilistic determination of the presence of pulmonary inflammation is generated.

In preferred embodiment of the invention, a probabilistic determination of the presence of chronic pulmonary inflammation is made through a two dimensional analysis wherein a percentage value for at least two cells types are plotted as the x and y axis of a graph with the z axis representing the probability of the condition. Preferably, percentage values of PMNs and macrophages are plotted to determine a probability of acute pulmonary inflammation, whereas, percentage values of lymphocytes and plasma cells are plotted to determine a probability of chronic pulmonary inflammation.

Most preferably, the computer calculates a probability score based on the combined x and y values described above.

The probability score represents a data point on a continuum. The score value increases when high percentages of mobile cells are detected and vice versa.

In a broad sense, the invention is a method of determining a presence of pulmonary inflammation, comprising the steps of examining a sputum sample with a microscope combined with an image acquisition system; acquiring images of cells in the sputum sample; analyzing the images of the cells with an image recognition system to detect at least two types of mobile cells; counting individual cells of each of the at least two types of mobile cells; generating at least two sums from the counts, each of the sums representing a number of individual cells; comparing each sum of at least two cell types to an average number of expected cells for each of the cell types; and generating a score based on the comparison, where the score is a probabilistic determination of a likelihood of inflammation.

The invention presents an improvement over the state of the art in many significant ways. First, rather than a "gestalt" approach to sputum analysis as is currently practiced in the art, the inventive system introduces a level of objectivity and reproducibility to the diagnosis of inflammation. Moreover, because the system produces an actual percentage of cells, a treating clinician is given the benefit of a baseline with which to compare subsequent test results.

DETAILED DESCRIPTION OF THE INVENTION

Figure 1:
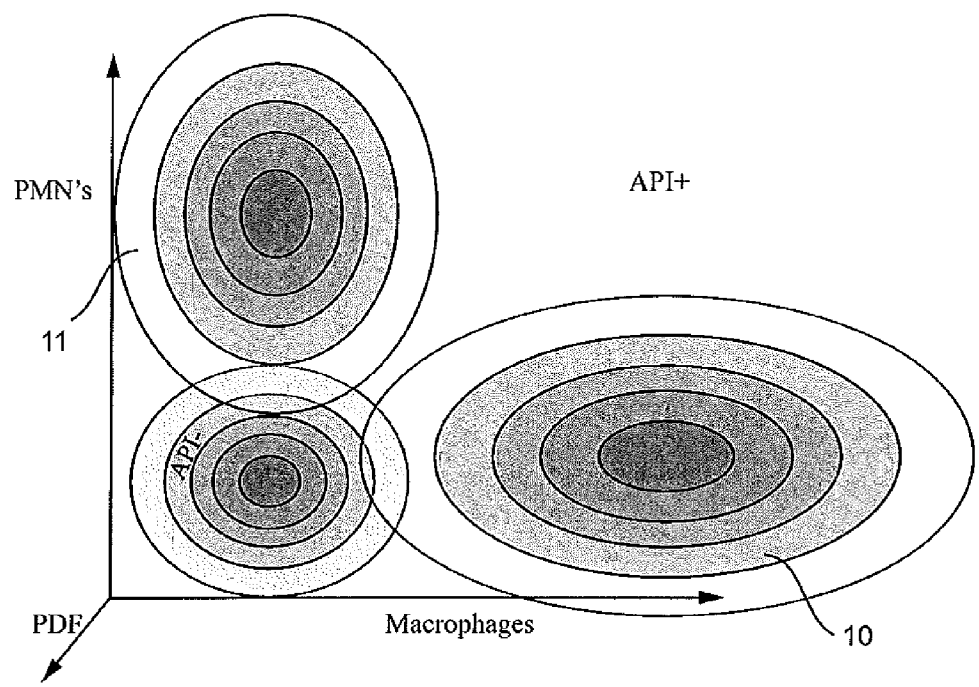
FIG. 1 is a schematic representation of a three-dimensional analysis for acute pulmonary inflammation according to an embodiment of the invention.

Embodiments of the present invention will now be described with reference to the above-identified figures of the Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As described, a sputum cytological specimen contains representative cells from a patient's lung tissue. The nature of the specimen is such that it is very difficult to manually analyze and it is especially difficult—if not impossible—to obtain quantitative cellular information. With computer analysis, however, statistics about the cellular population on a slide could be rapidly generated giving a clinician valuable information that would otherwise not be attainable.

In the inventive system a sputum sample is fixed and prepared on a slide in a manner known to one of skill in the art. However, instead of manually examining the slide, it is analyzed by a computer having specialized hardware and software to carry out the analysis of the invention.

In a preferred embodiment, a microscope combined with an image capture device incrementally moves across the slide capturing images of the slide at each increment. An image recognition system analyzing the captured images is trained to classify the cells of interest on a cell-by-cell basis and count how many cells of cell-types of interest are present.

One of ordinary skill in the art would know how to train an image recognition system to classify mobile cells based on well-known morphological characteristics. However, by way of example, the following are some morphological characteristics that may be examined PMNs are characterized by multi-lobed nuclei. Accordingly, in one embodiment, the image recognition system is trained to search for blobs of pixels that have some striation therein. Macrophages frequently contain intracytoplasmic phagocytized foreign material ("dust laden" in appearance). Accordingly, in one embodiment, the image recognition system is trained to search for multiple specks on a cell. Lymphocytes contain a thin rim of scant cytoplasm. Accordingly, in one embodiment, the image recognition system is trained search for lightly-stained cytoplasm. Plasma cells have eccentric nuclei. Accordingly, in an embodiment, the image recognition system is trained to measure the several nuclear radii and to determine whether it is generally round/elliptical or eccentric.

It will be understood that the cell classification and cell counting may be performed in real time—or at a time after the images are acquired. That is, as the image acquisition system acquires images of cells, various cell parameters are examined to determine cell type. Once a cell type is determined (assuming that it is a cell of interest), it is added to a running tally in temporary storage on a computer. Once images corresponding to the entire, or majority of a slide is acquired, it is stored as a digital image on a digital storage medium. Tallies of cells of interest also are stored on a storage medium—such as a computer hard drive.

Alternatively, as a first step, a slide is digitized and stored on a storage device. Thereafter, a computer, using an image recognition system analyzes the digitally stored images of cells to classify and quantify them according to the teachings of the invention.

A sputum cytology sample will typically contain a variety of mobile cells (both interstitial and blood cells) and local, structural cells. Specific mobile cells are implicated in inflammatory process and it is those cells that are of interest in determining inflammation. To that end, an image recognition system is trained to classify the mobile cells PMNs, macrophages, lymphocytes, plasma cells, eosinophils and mast cells. The computer will search for all of these cell types in each specimen and count how many of each of the cell types are present. The computer will then add the results of each of the tallies to arrive at a total number of mobile cells. Based on the tallies of individual mobile cells out of the total number of mobile cells—a percentage value is determined for each of the mobile cells. The percentages are then plotted to determine a likelihood of inflammation. For example, if PMNs are found to account for 75% (or more) of total cells and macrophages are found to account for 10% or more of total mobile cell population—a likelihood of acute inflammation is determined.

In a preferred embodiment, the ratios of two or more mobile cell types with respect to each other is used to determine a probability of inflammation—and the specific stage thereof. For example, if PMNs are found to account for 75% of total mobile cells and macrophages are found to account for 10% or more of total mobile cell population—such a ratio would indicate a presence of acute pulmonary inflammation. However, if PMNs accounted for only about 5% of total mobile cells and lymphocytes and plasma cells accounted for about 70% and 5%, respectively—such ratio would indicate a presence of chronic pulmonary infection.

In addition to the percentages of mobile cells extrapolated by the cell counts—the absolute number of cells may be utilized to generate a probability of inflammation. That is, based on data obtained from normal patients, an average number of mobile cells are determined. If the absolute number of at least two mobile cells of interest are higher than average—a probability of inflammation would be indicated. As the spread of cells above average increases, a score value correspondingly increases.

In an embodiment of the invention, the percentage measure and absolute number metric are combined. Specifically, if absolute cells numbers are found to be above a threshold number and the percentages of cells are within certain ratios—a probability of inflammation is determined.

Below are some examples of specific embodiments of the invention for determining each of acute and chronic pulmonary inflammation. In all embodiments mentioned below, the computer searches for PMNs, macrophages, lymphocytes and plasma cells. In some embodiments, the computer additionally searches for eosinophils and mast cells in order to determine a presence of allergic or asthmatic activity.

Acute Pulmonary Inflammation

EXAMPLE 1

A sputum sample is analyzed for a presence of PMNs, macrophages, lymphocytes and plasma cells. If PMNs are found to account for about 75-95% percent of such mobile cells and macrophages account for about 10-20% of such cells—a probability of acute pulmonary inflammation is determined.

Alternatively, if the absolute number of PMNs is from 50,000-500,000 cells and the absolute number of macrophages is from 10,000-100,000 cells, a probability of acute pulmonary inflammation is determined.

In one preferred embodiment, both the absolute numbers and percentages are plotted, whereby if both the percentages and the absolute numbers of PMNs and macrophages are within the above-cited ranges, a probability of acute pulmonary inflammation is determined.

FIG. 1, schematically shows a three-dimensional analysis of the invention. A high number of macrophages 10, may in itself indicate inflammation. However, it also is possible that there is no inflammation. Similarly, an elevated number of PMNs 11, may or may not be as a result of inflammation. However, when these two parameters are combined, patients that are positive for inflammation are distinguished from those that are negative—with a high degree of accuracy. That is, either increased absolute numbers of macrophages and PMNs, or increased percentages of these cells with respect to each other or with respect to other mobile cells—or some combination of the two metrics—will allow for discrimination between patients that are negative and those that are positive for inflammation.

EXAMPLE 2

A sputum sample is analyzed for a presence of PMNs, macrophages, lymphocytes, plasma cells and eosinophils. If PMNs account for about 75-95% percent of such cells, macrophages account for about 10-20% of such cells and eosinophils account for 2-4% of total mobile cells analyzed—a probability of acute pulmonary inflammation is determined. The presence of eosinophils may be present in such a range in the presence of an allergic or asthmatic condition.

Alternatively, if the absolute number of PMNs is from 50,000-500,000 cells, the absolute number of macrophages is from 10,000-100,000 cells and the absolute number of eosinophils is anywhere from 2,000-15,000 cells a probability of acute pulmonary inflammation is determined.

In one preferred embodiment, both the absolute numbers and percentages are plotted, whereby if both the percentages and the absolute numbers of PMNs, macrophages and eosinophiles are within the above-cited ranges, a probability of acute pulmonary inflammation is determined.

EXAMPLE 3

A sputum sample is analyzed for a presence of PMNs, macrophages, lymphocytes, plasma cells, eosinophils and mast cells. If PMNs account for about 75-95% percent of such cells, macrophages account for about 10-20% of such cells, eosinophils account for 2-4% of total mobile cells analyzed and mast cells account for than 1% of total mobile cells—a probability of acute pulmonary inflammation is determined. The presence of eosinophils may be present in such a range in the presence of an allergic or asthmatic condition.

Alternatively, if the absolute number of PMNs is from 50,000-500,000 cells, the absolute number of macrophages is from 10,000-100,000 cells and the absolute number of eosinophils is anywhere from 2,000-15,000 cells a probability of acute pulmonary inflammation is determined.

In one preferred embodiment, both the absolute numbers and percentages are plotted, whereby if both the percentages and the absolute numbers of PMNs, macrophages, eosinophiles and mast cells are within the above-cited ranges, a probability of acute pulmonary inflammation is determined.

Chronic Pulmonary Inflammation

EXAMPLE 1

A sputum sample is analyzed for a presence of PMNs, macrophages, lymphocytes and plasma cells. If lymphocytes are found to account for anywhere between 70-90% percent of such mobile cells and plasma cells are found to account for anywhere between 5-20% of such cells—a probability of chronic pulmonary inflammation is determined.

Alternatively, if the absolute number of lymphocytes is anywhere from 50,000-350,000 cells, and the absolute number of plasma cells is anywhere from 10,000-75,000 cells, a probability of chronic pulmonary inflammation is determined.

In one preferred embodiment, both the absolute numbers and percentages are plotted, whereby if both the percentages and the absolute numbers of lymphocytes and plasma cells are within the above-cited ranges, a probability of chronic pulmonary inflammation is determined.

Figure 2:
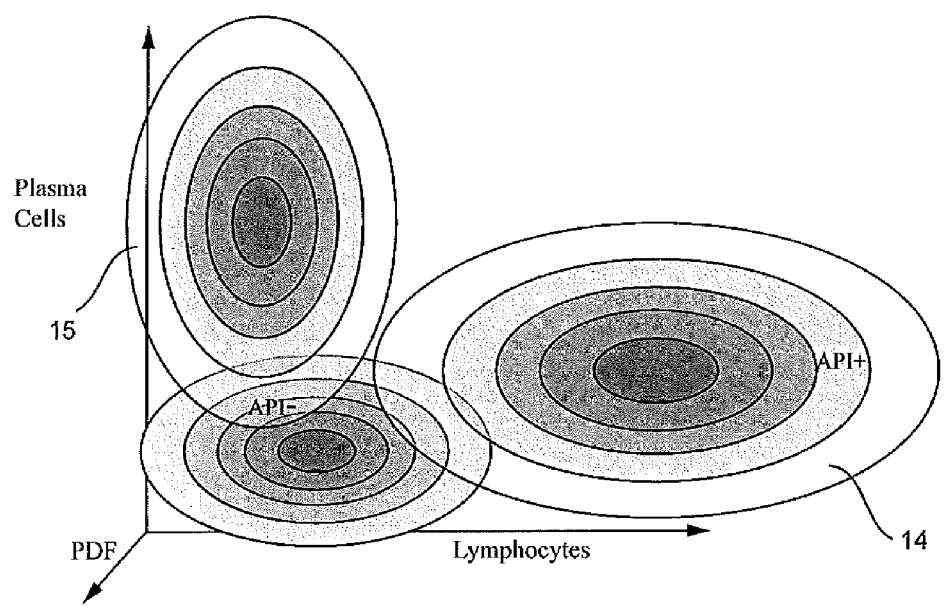
FIG. 2 is a schematic representation of a three-dimensional analysis for chronic pulmonary inflammation according to an embodiment of the invention.

FIG. 2, schematically shows a three-dimensional analysis of the invention. A high number of lymphocytes 14, may in itself indicate inflammation. However, it also is possible that there is no inflammation. Similarly, an elevated number of plasma cells 15 may or may not be as a result of inflammation. However, when these two parameters are combined, patients that are positive for inflammation are distinguished from those that are negative—with a high degree of accuracy. That is, either increased absolute numbers of lymphocytes and plasma cells, or increased percentages of these cells with respect to each other or with respect to other mobile cells—or some combination of the two metrics—will allow for discrimination between patients that are negative and those that are positive for inflammation.

EXAMPLE 2

A sputum sample is analyzed for a presence of PMNs, macrophages, lymphocytes and plasma cells. If lymphocytes are found to account for anywhere between 70-90% percent of such mobile cells, plasma cells are found to account for anywhere between 5-20% of such cells and PMNs are found to account for anywhere between 5-25% of mobile cells—a probability of chronic pulmonary inflammation is determined.

Alternatively, if the absolute number of lymphocytes is anywhere from 50,000-350,000 cells, the absolute number of plasma cells is anywhere from 10,000-75,000 cells and the absolute number of PMNs is anywhere from 10,000-100,000 cells, a probability of chronic pulmonary inflammation is determined.

In one preferred embodiment, both the absolute numbers and percentages are plotted, whereby if both the percentages and the absolute numbers of lymphocytes, plasma cells and PMNs are within the above-cited ranges, a probability of chronic pulmonary inflammation is determined.

EXAMPLE 3

A sputum sample is analyzed for a presence of PMNs, macrophages, lymphocytes, plasma cells and eosinophils. If lymphocytes are found to account for anywhere between 70-90% percent of such mobile cells, plasma cells are found to account for anywhere between 5-20% of such cells, PMNs are found to account for anywhere between 5-25% of mobile cells and eosinophils are found to account for anywhere between 2-4% of mobile cells—a probability of chronic pulmonary inflammation is determined.

Alternatively, if the absolute number of lymphocytes is anywhere from 50,000-350,000 cells, the absolute number of plasma cells is anywhere from 10,000-75,000 cells, the absolute number of PMNs is anywhere from 10,000-100,000 cells and the absolute number of eosinophils is anywhere between 10,000-100,0000 cells, a probability of chronic pulmonary inflammation is determined.

In one preferred embodiment, both the absolute numbers and percentages are plotted, whereby if both the percentages and the absolute numbers of lymphocytes, plasma cells, PMNs and eosinophils are within the above-cited ranges, a probability of chronic pulmonary inflammation is determined.

Figure 3:
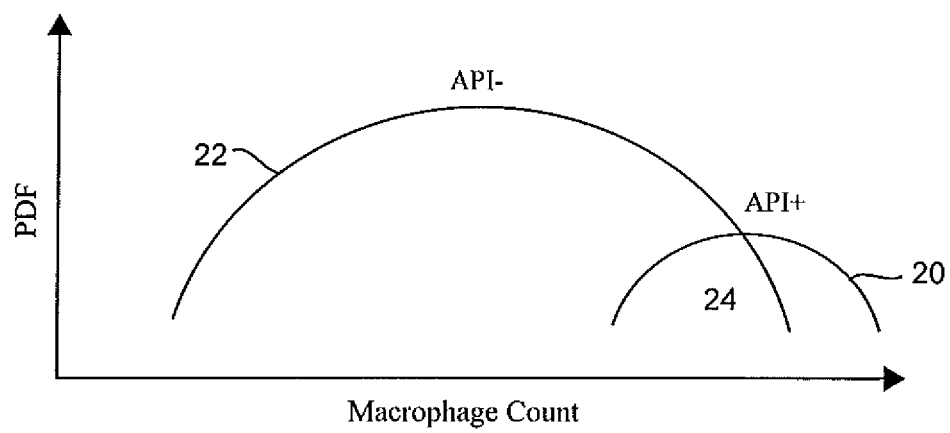
FIG. 3 is a schematic representation showing the shortcomings of two-dimensional analysis.

In a preferred embodiment, in order to yield a probability of inflammation, a minimum of two parameters are examined. For example, to determine a probability of acute chronic inflammation, the system will determine whether or not each of PMNs and macrophages are present at elevated levels. This is referred to as a three-dimensional analysis. Analysis of a single parameter (cell-type) may lead to over-calling inflammation. For example, referring to FIG. 3, which shows a plot of macrophages, Arc 20 shows a level of macrophages that may be associated with inflammation. Arc 22 shows a range of macrophages within which a patient may be negative for inflammation. In the area of overlap 24, a patient may be called positive for inflammation when, in fact, he/she is negative for the condition. The same is true for PMNs (although not shown). However, when the two parameters are combined (as shown in FIG. 1) patients with inflammation are separated from those that are negative.

It will be understood that the probability of inflammation can be a score, which represents a data point on a continuum. That is as the percentages of mobile cells of interest and/or the absolute numbers of cells increase—the score will correspondingly increase.

One possible way of displaying results of the computer analysis, is by way of histograms. For example, in an embodiment, histograms are presented having designated bins for each cell type. For instance, after classifying and quantifying cells a histogram having three distinct bins for lymphocytes, plasma cells and PMNs is generated. The presence of these three cell types may indicate a presence of chronic pulmonary inflammation. To further approximate whether such condition exists, each bin is examined to determine a percentage value for each mobile cell type out of the total number of mobile cells. If the ratios are found to be in the ranges described above, the slide will be deemed as "probable" for inflammation.

In a preferred embodiment, cell types are presented on the histogram only if a threshold number of that particular cell type is reached. For example, for PMNs a threshold may be set to 50,000. If less than 50,000 PMNs are detected—then PMNs are not included in the histogram.

Having described this invention with regard to specific embodiments, it is to be understood that the description is not meant as a limitation since further modifications and variations may be apparent or may suggest themselves to those skilled in the art. It is intended that the present application cover all such modifications and variation as fall within the scope of the appended claims.

What is claimed is:

1. A method of determining a presence of pulmonary inflammation, comprising the steps of:
   examining a slide comprising a sputum sample with a microscope combined with an image acquisition system;
   acquiring images of cells in said sputum sample;
   analyzing said images of said cells with an image recognition system to detect at least two types of mobile cells;
   counting individual cells of each of said at least two types of mobile cells;
   generating at least two sums from said counts, each of said sums representing a number of individual cells;
   comparing each of said sums to an average number of expected cells for each of said cell types; and
   generating a score based on said comparison, said score indicating a likelihood of inflammation.

2. The method of claim 1, wherein said at least two types of mobile cells comprise PMNs and macrophages.

3. The method of claim 1, wherein said at least two types of mobile cells comprise plasma cells and lymphocytes.

4. The method of claim 1, further comprising the step of adding the sums from said counts to generate a sum of combined mobile cells and determining a percentage value for each cell type, said percentage value representing a percentage of a mobile cell type out of a sum of combined mobile cells.

5. The method of claim 4, wherein percentage values for at least two cell types and sums of individual cell numbers of said at least two cell types are combined to generate said score.

* * * * *